United States Patent

Schülken et al.

[11] Patent Number: 5,556,371
[45] Date of Patent: Sep. 17, 1996

[54] DEVICE FOR TRANSANAL RESECTATE EXTRACTION

[75] Inventors: Heinrich Schülken, Stutensee-Staffort; Karl Schlipf, Karlsruhe, both of Germany

[73] Assignee: Kernforschungszentrum Karlsruhe GmbH, Karlsruhe, Germany

[21] Appl. No.: 303,751

[22] Filed: Aug. 18, 1994

Related U.S. Application Data

[63] Continuation-in-part of PCT/DE93/00124, Feb. 13, 1993.

[30] Foreign Application Priority Data

Feb. 22, 1992 [DE] Germany ............... 42 05 488.5

[51] Int. Cl.[6] ............... A61B 1/00; A61B 1/31
[52] U.S. Cl. ............... 600/201; 600/105; 600/106; 600/203; 600/213
[58] Field of Search ............... 600/101, 104–106, 600/114, 121, 123, 127, 129, 201, 203, 213; 606/49, 114, 167, 170, 185, 46, 205; 128/751

[56] References Cited

U.S. PATENT DOCUMENTS

| 752,828 | 2/1904 | Devine | 16/114 R |
|---|---|---|---|
| 1,952,617 | 3/1934 | Wappler | 128/303 |
| 2,113,246 | 4/1938 | Wappler | 128/321 |
| 2,532,043 | 11/1950 | Wallace | 128/7 |
| 3,149,633 | 9/1964 | Zingale | 606/46 |
| 4,132,227 | 1/1979 | Ibe | 128/4 |
| 4,538,594 | 9/1985 | Boebel et al. | 128/6 |
| 4,625,713 | 12/1986 | Hiraoka | 128/4 |
| 4,655,219 | 4/1987 | Petruzzi | 128/321 |
| 4,791,913 | 12/1988 | Maloney | 128/6 |
| 4,877,050 | 10/1989 | Harris | 137/315 |
| 4,998,527 | 3/1991 | Meyer | 128/6 |
| 5,282,800 | 2/1994 | Foshee et al. | 606/52 |
| 5,287,845 | 2/1994 | Faul et al. | 128/7 |
| 5,342,391 | 8/1994 | Foshee et al. | 606/205 |

FOREIGN PATENT DOCUMENTS

| 3329784 | 2/1985 | Germany. |
| 3823604 | 1/1990 | Germany. |
| 2130889 | 6/1984 | United Kingdom. |

Primary Examiner—Richard J. Apley
Assistant Examiner—Kelly McGlashen
Attorney, Agent, or Firm—Klaus Bach

[57] ABSTRACT

In a device for transanal resectate extraction which includes a rectoscope sleeve with a proximal tubular end portion, a connecting piece sealingly mounted onto said tubular proximate end portion for closing the rectoscope sleeve and including a bore axially extending therethrough and a resectate extractor having a tubular portion extending through the bore so as to be axially movable but position-lockable therein. The tubular portion of the extractor has a protector portion at its distal end with an axial passage in alignment with the tubular extractor portion for receiving grasping pincers inserted through the tubular extractor portion. The protector portion has an outer diameter smaller than the inner diameter of the rectoscope sleeve so that it can be retracted into the sleeve.

10 Claims, 2 Drawing Sheets

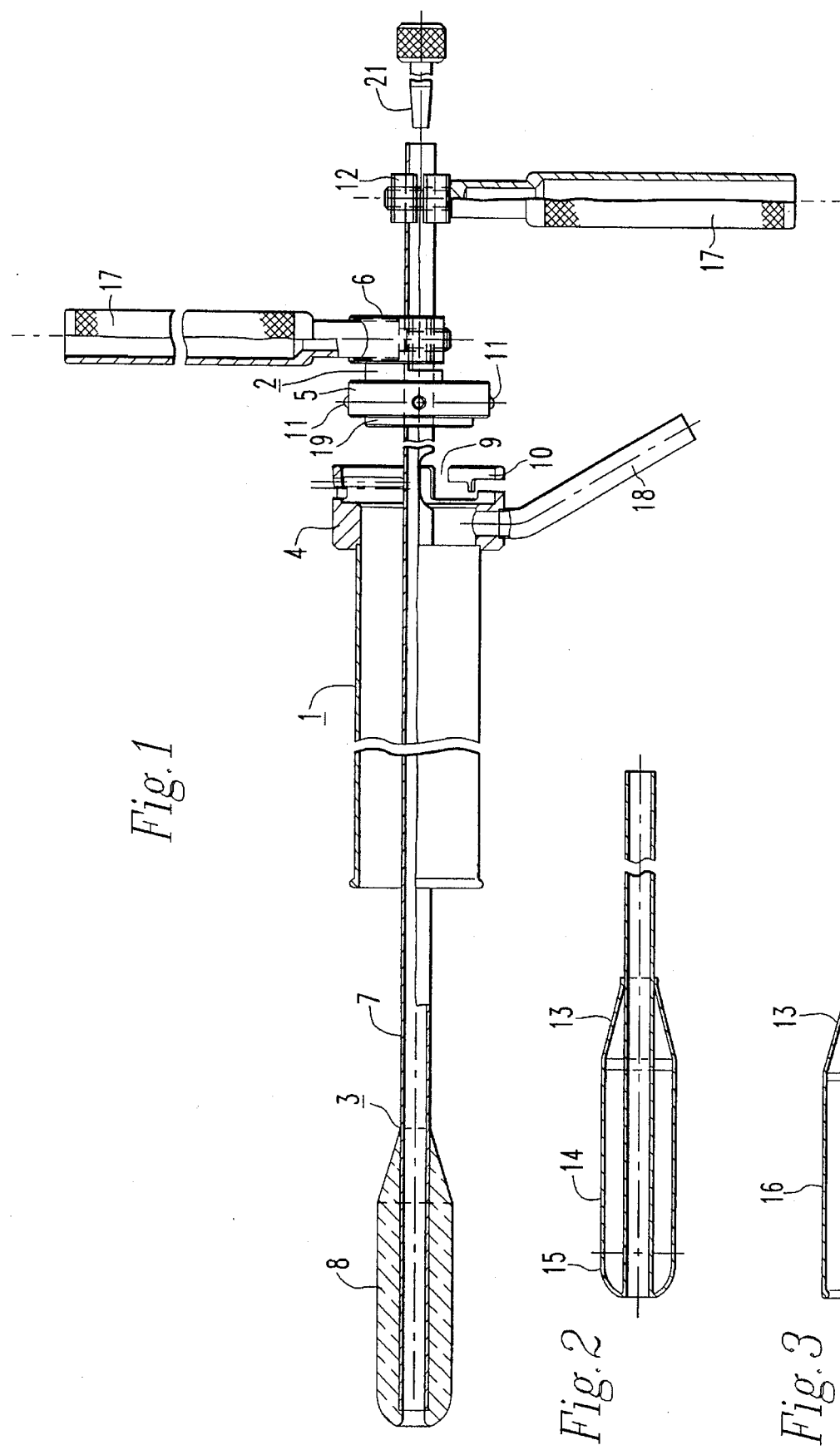

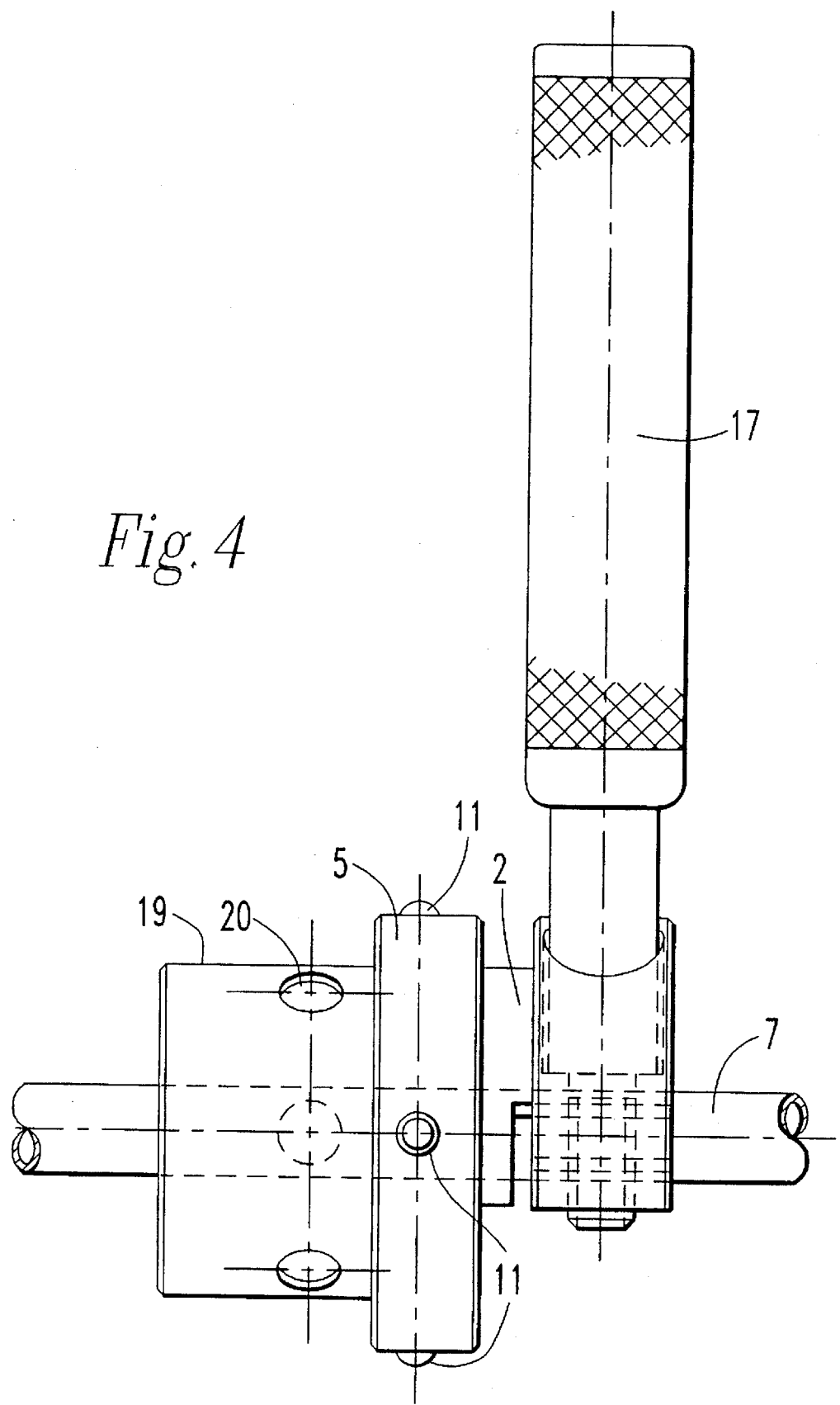

DEVICE FOR TRANSANAL RESECTATE EXTRACTION

This is a continuation-in-part application of international application PCT/DE93/00124 filed Feb. 13, 1993 and claiming priority of German application P 42 05 488.5 of Feb. 22, 1992.

BACKGROUND OF THE INVENTION

The invention relates to a device for transanal rectum extraction comprising a rectoscope sleeve with a tubular end portion and a resectate extractor extending through the end section and the sleeve for retracting resectate into the rectoscope sleeve.

Neoplasm (the growth of new tissue such as a tumor) and angiodysplasm (the formation of vessels) in the sigma intestinal area may require resection of this portion of the intestines between the colon descendens and the rectum. With such a resection the intestine is cut in front of and behind the sigma per laparoskopiam by means of optical and surgical instruments inserted through the abdominal wall. Before the colon descendens and the rectum can be interconnected the resectate has to be removed. The resectate is extracted by way of the anus.

For the extraction of the resectate a rectoscope sleeve is usually inserted transanorectally and the proximal end thereof, that is, the end near the operator, is closed by a connecting piece. Rectoscope sleeves with an outer diameter of 40 mm and of various lengths are commercially available. The known rectoscope sleeves are inclined at their distal end, that is, the end remote from the operator. They are inserted with the aid of a so-called mandrin which is a rod with a thickened end portion in the shape of a cone or a rounded cylinder at the distal end whose diameter is slightly less than the inner diameter of the rectoscope sleeve. The connecting piece of the rectoscope sleeve includes a pipe nozzle through which carbon dioxide may be introduced for expanding the intestine. Through an opening in the connecting piece a pair of grasping pincers is advanced through the rectoscope sleeve into the rectum. The laparascope operator passes the resectate onto the grasping pincers by which it is removed transanally through the resectate sleeve.

Such a rectoscope sleeve with a connecting piece is shown in FIG. 1 of DE 33 29 784 C2. Furthermore there is shown a pair of grasping pincers which is inserted through the connecting piece into the rectoscope sleeve.

During transanorectal insertion of the grasping pincers into the abdomen with the described procedure—depending on the anatomy and histology of the intestine portion which is not protected by the rectoscope sleeve and depending on the experience of the surgeon and the design of the grasping pincers—lesions and/or perforations are possible.

DE 38 23 604 A1 discloses an apparatus for the intracavity irradiation of malignant colon tumors. The apparatus shown therein includes a tubular structure corresponding to a rectoscope sleeve and an insertion member consisting of a tube with a club-like thickened end. The club-like thickened end is hollow so that radioactive material can be supplied to a point adjacent the area to be treated.

Further, DE 82 33 240 U1 discloses a rectoscope which includes a short, wide, tubular structure with a rotatable connecting ring. A mandrin extends through the tubular structure. After removal of the mandrin, as a connecting piece an instrument carrier is placed onto the tubular structure and is connected thereto by means of a bayonet type fitting. Locking is achieved by the engagement of locking balls in an annular groove.

It is the principal object of the present invention to provide an improved device with which an intestine section can be extracted transanally with relatively little chance for lesions or perforations of tissue and wherein such extractions can be performed requiring only simple and rapid manipulations by the surgeon.

SUMMARY OF THE INVENTION

In a device for transanal resectate extraction which includes a rectoscope sleeve with a proximal tubular end portion, a connecting piece sealingly mounted onto said tubular proximate end portion for closing the rectoscope sleeve and including a bore axially extending therethrough and a resectate extractor having a tubular portion extending through the bore so as to be axially movable but position-lockable therein, the tubular portion of the extractor has a protector portion at its distal end with an axial passage in alignment with the tubular extractor portion for receiving grasping pincers inserted through the tubular extractor portion, and the protector portion has an outer diameter smaller than the inner diameter of the rectoscope sleeve so that it can be retracted into the sleeve.

BRIEF DESCRIPTION OF THE DRAWINGS

FIG. 1 shows the device according to the invention;

FIG. 2 shows one embodiment of a resectate extractor;

FIG. 3 shows another embodiment of the resectate extractor; and

FIG. 4 shows an advantageous embodiment of a connecting piece for the device.

DESCRIPTION OF A PREFERRED EMBODIMENT

The device according to the invention comprises essentially three components: a rectoscope sleeve 1, a connecting piece 2 and a resectate extractor 3.

The rectoscope sleeve 1 may be a tube whose diameter is adapted to the diameter of the anus. The length of the rectoscope sleeve without end portion 4 generally corresponds to the length of the rectum (about 15 to 20 cm). In order to avoid traumatization of the inner wall of the rectum during insertion, the distal end of the rectoscope sleeve is preferably rounded, that is, provided with a bead. For the same reason an embodiment of the rectoscope sleeve having a distal end formed in rotational symmetry appears to be better suitable than the known rectoscope sleeves. But the rectoscope sleeve may also be inclined at its distal end in the known manner. The proximate end of the rectoscope sleeve is formed by the tubular end portion 4. The outer diameter of the end portion 4 is preferably larger than the outer diameter of the rectoscope sleeve as such in order to provide more space for the bore which receives the resectate extractor 3 and for additional bores and the instruments (grasping pincers) to be introduced therethrough. One of the additional bores can be used for the introduction of an optical control device in a manner as generally known.

Preferably a gas inlet nozzle 18 is provided at the end portion 4 of the rectoscope sleeve 1. This facilitates mounting and removal of the connecting piece 2 as, in that case, it is not connected to a gas supply line. An arrangement is particularly preferred in which the gas inlet nozzle 18 is made in the form of a handle such as a knurled sleeve. Such a handle may be connected during the operation, for example, by means of an adjustable hinged bracket to the operating table is necessary. With the connecting piece 2 the rectoscope sleeve 1 can be sealed at its end portion 4. A sealed closure is necessary in order to prevent uncontrolled release of the gas (carbon dioxide) introduced during the operation.

The connecting piece 2 preferably comprises a cylinder 5 and a U-shaped clamping structure 6. The cylinder 5 includes an axial bore around which the clamping structure 6 is disposed. In order to facilitate mounting of the connecting piece 2 onto the end portion 4 of the rectoscope sleeve 1 (shown unmounted in FIG. 1) without cogging, the distal side of the cylinder 5 is provided with a guide tube 19 arranged in an axially symmetric manner. A particularly advantageous embodiment of such a guide tube has a length which is so selected that it extends through the end portion 4 up to the tubular portion of the rectoscope sleeve. With such an arrangement cogging of the connecting piece can be safely avoided. FIG. 4 shows such an arrangement of the connecting piece 2. The guide tube 19 includes openings 20 which are so arranged that the passage for the gas inlet nozzle 18 remains open when the connecting piece 2 is firmly mounted on the rectoscope sleeve 1.

Preferably, the rectoscope sleeve 1 and the connecting piece 2 are interconnected by means of a bayonet connection. In this embodiment the outer surface of the cylinder 5 is provided with at least two but preferably three pins 11 which are engaged in a corresponding amount of angled cut-outs 9 formed in the end of the end portion 4. The cut-outs provide for resilient webs 10 at the edge of the end portion 4. The resilient webs 10 may have a recess of about 0.1 mm at one particular location and adjacent thereto a stop by which a definite locking position for the pins is defined. This is particularly advisable if the guide tube 19 has the shape as shown in FIG. 4 in order to provide for alignment of the openings 20 with the gas supply nozzle.

The most important part of the invention is represented by the resectate extractor. The purpose of the resectate extractor is to guide the grasping pincers by which the resectate is held and to position it in the proper location. It is advanced anorectally until its distal end projects from the remaining part of the intestine. This end of the resectate extractor is so shaped that, during its advancement through the rectum, traumatization, particularly lesions and perforations of the intestinal wall, can be avoided.

As mentioned earlier, in the devices known so far, the grasping pincers are inserted through an opening in the connecting piece into the rectoscope sleeve and advanced through the sleeve into the intestine. However the end of a grasping pincer can be formed atraumalically only to a limited extent since it has to be moved through an opening in the connecting piece without essential clearance in such a manner that the opening can be sealed. Also, the movable parts at the distal end of the grasping pincers need to remain free so that it requires substantial skill for the surgeon to advance such an instrument to the desired location without injuring the intestine walls.

By the resectate extractor according to the invention those difficulties are overcome. The resectate extractor is shaped in such a way that the surface pressure between the instrument and the intestinal walls, which, with excessive values finally leads to the perforation of the intestinal walls, is reduced to non-critical values so that safe gliding over intestinal wall irregularities is facilitated. During this procedure the pressure on the intestinal walls can further be reduced by increasing the pressure of the $CO_2$ supplied to the rectoscope sleeve via the gas inlet nozzle 18 to a value slightly above the pneumoperitoneum pressure in order to expand the rectum and partially lift it of the outer surface of the protector portion 8.

Only when the resectate extractor is in its desired position the end plug 21 is removed and the grasping pincers are inserted and moved forward through the tube portion 7 and the protector portion 8 of the resectate extractor 3 into the abdomen where the resectate is grasped by the grasping pincers. In this manner, traumatization of the rectum by the grasping pincers becomes impossible.

When the surgeon has grasped the resectate with the grasping pincers the grasping pincers are retracted together with the resectate extractor. The resectate is removed from the rectoscope sleeve in the usual manner by removing the connecting piece.

Two embodiments of the resectate extractor are presented here. In both embodiments the resectate extractor consists of a tube portion 7 with a tubular protective distal end portion 8 of increased diameter with respect to the tube portion.

In the embodiment of FIG. 2 the tubular protective distal end portion is widened in the shape of a club. The tube portion 7 changes over, via a transition portion 13, to an essentially cylindrical portion 14 with increased outer diameter which carries at its distal end a semispherical end portion 15 with an opening for the grasping pincers. This embodiment provides for minimal surface pressure. The length of the transition portion 13 and the cylindrical portion 14 as well as the cone angle of the transition portion are so selected that the body is as streamlined as possible. The lengths of the three portions 13, 14, 15 should be less than the length of the rectoscope sleeve so that the resectate can be retracted into the rectoscope sleeve. It is also possible to eliminate the cylindrical portion 14 or to form the protector portion in the shape of a paraboloid.

The second embodiment which is shown in FIG. 3 is particularly suitable for the resection of infectuous or abnormal tissue. In this embodiment the tube portion 7 at the distal end of the resectate extractor can be widened funnel-like. Following the funnel-like expansion in the transition portion 13 there may be a cylindrical portion 16 whose outer as well as inner diameters are larger than the diameter of the tube portion 7. The distal edge of this resectate extractor is provided with a bead of somewhat increased thickness but which, at the end is drawn-in somewhat to form an end portion with which injuries to the intestinal walls can be avoided. With this embodiment it is possible to retract the resectate with the grasping pincers into the interior of the cylindrical portion 16 so that the inner wall of the rectum is not contacted by the resectate tissue when the resectate extractor is pulled back.

Handling of the device according to the invention is much facilitated in a displaceable clamping structure 12 is mounted on the tube portion 7 of the resectate extractor 3 which is disposed outside the rectoscope sleeve 1. Preferably the clamping structure 6 mounted on the connecting piece 2 and the clamping structure 12 mounted on the tube portion 7 are essentially of the same design.

Operating the clamping structures is particularly easy if they include a U-shaped part extending around the tube portion 7 and the legs of the U-shaped part are provided with bores of which one is threaded. The handle 17 of the clamping structures has a threaded end which passes through the non-threaded bore and is threaded into the threaded bore of the one leg of the U-shaped part so that the clamping forces can be generated by rotating the handle 17. Preferably the handle is in the form of a sleeve whose outer surface is knurled. Such hollow handle structure makes the handle substantial lighter thereby increasing the sensitivity in handling. The arrangement also permits operation of the clamping structures with one hand.

When the grasping pincers are not inserted into the resectate extractor the proximal end of the resectate extractor can be closed by an end plug 21 with a silicon cone. If the grasping pincers are inserted the resectate extractor tube portion 7 is sealed by the grasping pincers structure or by sealing elements associated therewith.

As material for the device according to the invention stainless steel is particularly suitable. Then the whole device can be sterilized in a simple manner wherein sealing means may consist of throw-away articles. However the protector portion of the resectate extractor may consist of polytetratfluoroethylene (PTFE) as shown in FIG. 1. PTFE is tissue compatible and water repellent and can also be sterilized at high temperatures. But it is also possible to make the device according to the invention or parts thereof such as the resectate extractor of plastic by an injection molding procedure and to discard those parts after use.

What is claimed is:

1. A device for transanal resectate extraction comprising:
   a) a rectoscope sleeve with a proximal tubular end portion,
   b) a connecting piece sealingly but removably mounted onto said proximal tubular end portion of said rectoscope sleeve for closing said rectoscope sleeve and including a bore extending parallel to the axis of said rectoscope sleeve,
   c) a resectate extractor having a tubular portion extending through said bore and having a distal end with a protector portion comprising a cylindrical portion with a semispherical end and a conical transition portion between said cylindrical portion and said tubular portion, said tubular portion being axially slidable in said bore in essentially sealing relationship therewith, said protector portion having an axial passage of a diameter corresponding to the inner diameter of said tubular portion and having an outer diameter smaller than the inner diameter of said rectoscope sleeve so as to be capable of being received therein and at least as large as the outer diameter of said tubular portion, said axial passage receiving grasping pincers such that they are movable forwardly through said tubular portion and through said protector portion for grasping resectate and holding it while said protector portion with said grasping pincers and the resectate grasped thereby is retracted into said rectoscope sleeve.

2. A device according to claim 1, wherein said proximal tubular end portion of said sleeve includes at least two angled cut-outs extending circumferentially and forming resilient cantilevered webs and said connecting piece is a cylindrical member with an axial bore and having at its outer surface at least two radial pins adapted to be received in said cut-outs for mounting said connecting piece onto said tubular end portion of said rectoscope sleeve and said connecting piece further has a guide tube axially extending therefrom and having a length so selected that it extends through the end portion and into the tubular portion of said rectoscope sleeve so as to prevent cogging of the connecting piece upon its assembly onto said tubular end portion.

3. A device for transanal resectate extraction comprising:
   a) a rectoscope sleeve with a proximal tubular end portion,
   b) a connecting piece sealingly but removably mounted onto said proximal tubular end portion of said rectoscope sleeve for closing said rectoscope sleeve and having a bore extending parallel to the axis of said rectoscope sleeve,
   c) a resectate extractor having a tubular portion extending through said bore and having a distal end with a protector portion, said tubular portion being axially slidable in said bore in essentially sealing relationship therewith, said protector portion having an axial passage and having an outer diameter smaller than the inner diameter of said rectoscope sleeve so as to be capable of being received therein and at least as large as the outer diameter of said tubular portion, and
   d) said connecting piece having a proximal side opposite said rectoscope sleeve and being provided at its proximal side with a U-shaped clamping structure extending around the bore for engaging said tubular portion extending through said bore.

4. A device for transanal resectate extraction comprising:
   a) a rectoscope sleeve with a proximal tubular end portion,
   b) a connecting piece sealingly but removably mounted onto said proximal tubular end portion of said rectoscope sleeve for closing said rectoscope sleeve and having a bore extending parallel to the axis of said rectoscope sleeve,
   c) a resectate extractor having a tubular portion extending through said bore and having a distal end with a protector portion, said tubular portion being axially slidable in said bore in essentially sealing relationship therewith, said protector portion having an axial passage and having an outer diameter smaller than the inner diameter of said rectoscope sleeve so as to be capable of being received therein and at least as large as the outer diameter of said tubular portion, and
   d) a U-shaped clamping structure mounted on said tubular portion so as to be slidable thereon but engageable therewith.

5. A device according to claim 3, wherein said U-shaped clamping structure includes legs with aligned bores extending through said legs, one of said bores being threaded, and a handle with a threaded end extends through the nonthreaded bore and is threaded into said one bore for clamping said legs upon turning of said handle.

6. A device according to claim 4, wherein said U-shaped clamping structure includes legs with aligned bores extending through said legs, one of said bores being threaded, and a handle with a threaded end extends through the nonthreaded bore and is threaded into said one bore for clamping said legs upon turning of said handle.

7. A device according to claim 5, wherein said handle has a knurled outer surface.

8. A device according to claim 7, wherein said handle has a knurled outer surface.

9. A device according to claim 1, wherein said proximal tubular end portion of said rectoscope sleeve is provided with a nozzle for supplying gas to said rectoscope sleeve.

10. A device according to claim 9, wherein said nozzle is in the shape of a handle to facilitate handling of said rectoscope sleeve.

* * * * *